United States Patent [19]
Spani et al.

[11] Patent Number: 5,363,848
[45] Date of Patent: Nov. 15, 1994

[54] VARIABLE ILLUMINATION OF A LUMEN FOR ACOUSTIC BLOOD FLOW MEASUREMENT

[75] Inventors: Wayne M. Spani; William S. Kemper, both of San Diego, Calif.

[73] Assignee: Triton Technology, Inc., San Diego, Calif.

[21] Appl. No.: 977,142

[22] Filed: Nov. 16, 1992

[51] Int. Cl.$^5$ .............................................. A61B 8/06
[52] U.S. Cl. .............................. 128/661.09; 73/861.25
[58] Field of Search ......... 128/660.06, 661.08–661.10, 128/662.04; 73/861.25

[56] References Cited

U.S. PATENT DOCUMENTS

| | | | |
|---|---|---|---|
| 4,431,936 | 2/1984 | Fu et al. | 128/662.04 X |
| 4,841,492 | 6/1989 | Russell | 128/660.06 X |
| 4,852,576 | 8/1989 | Inbar et al. | 128/660.06 |
| 4,867,167 | 9/1989 | Magnin | 128/660.06 |
| 5,052,394 | 10/1991 | Carpenter et al. | 128/660.06 |
| 5,085,220 | 4/1992 | Nudell et al. | 128/662.04 X |
| 5,095,909 | 3/1992 | Nakayama et al. | 128/660.06 |

Primary Examiner—Francis Jaworski
Attorney, Agent, or Firm—William C. Fuess

[57] ABSTRACT

In an acoustic flowmeter of the transit time or Doppler type the electro/acoustic, and/or acousto/electric, gain of one or more elongate acoustic transducers is varied spatially along the length of the transducer. When the transducer(s) are situated across the width of a lumen that is both flowing fluid and surrounded by material that attenuates sound differently that does the fluid during acoustic fluid flow measurement, the differing transducer(s') gain(s) serves to compensate for differing acoustic attenuations in different acoustic paths. Particularly during in-vivo acoustic blood flow measurement, the non-uniform acoustic gain(s) serves to compensate for the differing acoustic attenuations of blood and tissue, commonly fat, surrounding a blood vessel, and to produce a more accurate measurement of blood flow.

27 Claims, 5 Drawing Sheets

VARIABLE ILLUMINATION OF A LUMEN FOR ACOUSTIC BLOOD FLOW MEASUREMENT

REFERENCE TO RELATED APPLICATIONS

The present patent application is related to U.S. patent application Ser. No. 07/997,143 entitled COMPACT X-CROSS TRANSDUCER ARRAY FOR A TRANSIT TIME FLOWMETER, PARTICULARLY FOR USE DURING IN-VIVO BLOOD FLOW MEASUREMENT, filed on an even date with the present application. The related application are to the same inventors as is the present application.

BACKGROUND OF THE INVENTION

1. Field of the Invention

The present invention generally concerns the acoustic measurement of fluid flow velocity, including in-vivo measurement of blood flow in animals.

The present invention particularly concerns a modification to the selective, regional, electro/acoustic or acousto/electric gain of at least one acoustic transducer of an acoustic flowmeter of either the transit time or Doppler types. The regionally variable gain compensates for differing acoustic attenuations that are presented to different portions of an acoustic path proceeding to and from the transducer(s) through both (i) the fluid for which dynamic flow is measured and (ii) material surrounding the flowing fluid.

2. Description of the Prior Art

2.1 Desirable Properties of an Acoustic Flowmeter, Particularly for Blood Flow Analysis An acoustic flowmeter would preferably permit direct measurement of the rate of fluid flow regardless of the dimensions of a conduit, or lumen, within which the fluid flows. An implantable acoustic flowmeter for blood flow measurement would preferably permit direct measurement of the rate of blood flow regardless of vessel dimensions or any change in dimensions during the period of measurement.

An acoustic flowmeter would preferably be accurate. An implantable blood flowmeter would exhibit accuracy over the period of a long-term in-vivo implant.

An acoustic flowmeter would preferably permit direct measurement of the rate and the volume of fluid flow regardless of the profile of the velocity of the flowing fluid, e.g. turbulent flow or stratified flow, within the conduit of lumen. An acoustic flowmeter for blood flow measurement would preferably permit direct measurement of the rate and the volume of blood flow regardless of the stratified velocity profile of blood flowing within a blood vessel.

An acoustic flowmeter would desirably be insensitive to the angular alignment between a lumen or conduit and a flow sensor. An acoustic flowmeter for blood flow measurement would preferably be insensitive to the angular alignment between a blood vessel and a flow sensor axis.

An implantable acoustic flowmeter for blood flow measurement would preferably be operative with a non-constrictive flow probe, useful on various sizes of vessels, pulsating arteries, veins, growing vessels or even groups of vessels.

2.2 Exemplary Acoustic Flowmeters for Blood Flow Analysis

An early ultrasonic blood flowmeter was designed and built in the USA by Franklin, Baker, Ellis, and Rushner, in 1959. It employed a transit-time technique to measure fluid flow velocity. Transit time acoustic flow measurement is now widely used to measure liquid flow in industry but has not been widely used until recently for in-vivo measurement of blood flow.

U.S. Pat. Nos. 3,575,050 and 3,906,791 to Lynnworth describe a number of transit time flowmeters and transducers. Lynnworth's preferred transducers were piezoelectric elements that (i) subtended the full width of a lumen, or blood vessel, and (ii) uniformly acoustically illuminated the entire cross section of fluid flow. Lynnworth placed his transducers both at the two ends of simple acoustic paths directed obliquely across the lumen, and at the two ends of longer acoustic paths that underwent several reflections. Industrial acoustic transit time flowmeters based on the Lynnworth patents are still being manufactured, in 1992, by Panametrics, Inc., of Waltham, Mass., U.S.A.

Rader later alleged that when the full cross-sectional area of a blood vessel was acoustically illuminated with a constant level of ultrasound then the volume of blood flow within the vessel could be measured with a transit-time system independently of the vessel area. Reference R. D. Rader. "A Diameter-Independent Blood Flow Measurement Technique", Medical Instrumentation, Vol 10 pp. 185–188 (1976). Rader's electronic implementation, however, suffered from an unstable zero-flow offset.

Some time later Drost wrote about the physical principles of a transit-time volume flowmeter, and developed certain electronic circuitry. Reference C. J. Drost, "Vessel Diameter-Independent Volume Flow Measurements Using Ultrasound", Proc. San Diego Biomed. Symp. San Diego, Calif.: Vol. 17, pp. 299–302 (1978).

This flowmeter became the subject of U.S. Pat. Nos. 4,227,407 for "Volume Flow Measurement System" and 4,391,124 for an Electroacoustic Transducer Calibration Method and Apparatus", assigned to Cornell Research Foundation, Inc. (1980).

Under support of the National Institute of Health (NIH), the Drost flowmeter was put through a program of in-vivo use and validation by physiologists at Cornell University, Ithaca, N.Y. Linearity, long-term stability, and a low and stable zero-offset were stated to have been obtained. A commercial version of this flowmeter is now marketed by Transonic Systems, Inc. as Transonic Model T101.

2.3 General Theory of the Operation of a Prior Art Transit-Time Flowmeter

The discussion, and the referenced drawings, of prior art acoustic flowmeters contained within this section is partly derived from the article "Ultrasonic Flowmeter Uses Wide-Beam Transit-Time Technique" by R. G. Burton and Dr. R. C. Gorewit appearing in Medical Electronics, Vol. 86, No. 2, at pages 68–73 (1984).

Early, conventional, transit-time flowmeters illuminated only a segment of the flow, sensing the flow velocity in that segment. The relatively more recent wide-beam transit-time flowmeters evenly illuminate the full cross-section of the vessel. Reference, for example, the double transducer, direct path, configuration of a prior art transit time flowmeter shown in FIG. 1. The transit-time of the ultrasound is then independent of the vessel dimensions. It is supposed to permit the sensing of the volume, as well as the velocity, of the flow directly. Reference Drost, op cit.

The signal of the flow probe shown in FIG. 1 is a function of the angle between sound beam and flow axis; it is thus sensitive to blood vessel misalignment. This problem is largely solved in the prior art modified transit-time double-transducer reflected-path flowmeter diagrammed in FIG. 2. In this prior art flowmeter configuration the fluid flow path is traversed twice along a reflective acoustic pathway. If the lumen is inclined relative to the transducer(s) than one acoustic path through the lumen will be at a relatively steeper angle over a relatively shorter distance while the second, reflected, portion of the path will be at a relatively shallower angle over a relatively longer distance. This geometry results in a first order correction to any signal error due to misalignment between the flow, or lumen, axis and the axis of the transducer sensor. The reflector, in the form of an L-shaped bracket, also serves to hold the vessel within the acoustic path.

Although Doppler acoustic flowmeters operate on a different principle then do transit time flowmeters, a Doppler flowmeter also exhibits sensitivity to misalignment. The transducer configuration of a prior art single-transducer Doppler acoustic flowmeter is diagrammed in FIG. 3, and the transducer configuration of a prior art dual-transducer Doppler acoustic flowmeter is diagrammed in FIG. 4.

An previous electrical instrumentation scheme for a transit time acoustic flowmeter is shown in schematic block diagram in FIG. 5. In this scheme both upstream and downstream transit-time measurements are made alternately. The circuit uses a master oscillator (for a time base) and memory elements (to store transit-time information). The timing circuitry first energizes one of the transducers to emit an acoustic signal, after which time the other transducer is connected to the receiver. The received acoustic signal, containing the full flow information, is transduced into an electrical signal, amplified and fed into a circuit which measures the phase difference between the received signal and the master oscillator signal. This phase difference is indicative of the time of transit, and thus of the rate of fluid flow. The average phase-shifted received signal is used to update one of two memory elements.

After waiting to let all acoustic echoes die out, the roles of transmitting and receiving transducer are reversed for a measurement of transit-time in the opposite upstream/downstream direction. The resulting phase shift is again stored, now in the other memory element. The difference between the two stored values is representative of the difference in acoustic propagation upstream and downstream in the flowing fluid, and thus of the rate of fluid flow. This sequence of measurements is repeated at intervals shorter than the fluid can appreciably change velocity, typically every few milliseconds.

An electronic zero-flow reference signal is generated by subtracting two consecutive upstream phase measurements, rather than an upstream and a downstream measurement. This eliminates the need for clamping the vessel to establish a zero-flow baseline. A crystal-controlled internal factor reference transit-time delay to read out directly in ml/min.

2.4 The Particular Theory of Operation of a Prior Art Transit-Time Flowmeter

The transit-time of a sound wave traveling between two transducers is a function of the velocity of the sound-conducting medium times the acoustic path length. This established method of measuring flow velocity in liquids and gases was implemented for biomedical use by Plass, among others. Reference Plass, K.G.; A new ultrasonic flowmeter for intravascular application. IEEE Trans. Bio-Med. Eng., vol. BME-11, pp. 154-156, Oct, 1964. Plass's intravascular system used the difference in transit time between an upstream and downstream projected sound burst to measure flow velocity with known zero reference. Rader, et al. used the same detections scheme for an extra-vascular flowmeter. Reference Rader, op cit. A noted drawback of the implementations of Plass and of Rader, et al. is the path-length-sensitivity of the transit-time technique: an error in vessel inside diameter estimation produces a proportional error in volume flow output.

Drost alleged that the diameter sensitivity of the acoustic transit-time measuring technique could be turned into a major advantage, providing direct volume flow metering capability. Drost alleged that his detection scheme and probe design produced true volumetric output for a wide range of vessel diameters with one size of flow probe, independent of flow profile.

2.5 Prior Art Probe Design for a Transit-Time Flowmeter

Drost describes in the aforementioned U.S. Pat. Nos. 4,227,407 and 4,391,124 that a rectangular beam of ultrasound, uniform in intensity across its height (dimension h in FIG. 1) is essential to producing a flowmeter output that is indicative not only of flow rate, but also of flow volume. Producing such a field is an empirical procedure. The acoustic field intensity of finite-sized ceramic transducers fall off towards the transducer edges. Lynnworth, who appreciated the utility of uniform illumination of a lumen even before Drost, recognized this small non-uniformity in transducers. In Lynnworth's U.S. Pat. No. 3,906,791 for an "Area Averaging Ultrasonic Flowmeter" he discusses "shading" the transducer electrodes to compensate for the weakened acoustic field at the edges of the acoustic beam emitted by the transducer. Reference also the earlier patent of Lynnworth U.S. Pat. No. 3,575,050 for a "Fluid Flowmeter".

The prior art, as exemplified by both Lynnworth and Drost, shows and describes that the acoustic illumination of a lumen for the transit time measurement of fluid flow rate and also, particularly, of fluid flow volume, should be uniform. The present invention will be seen to teach, and function, contra. One problem with uniform acoustic illumination plagues both transit time and Doppler acoustic flowmeters, and flow probes, in any environment, as is common, where material located proximately to, or surrounding, the flowing fluid within the lumen attenuates sound differently than does the fluid itself. The existence of such material is all but inevitable in, for example, in-vivo acoustic blood flow measurement where a blood vessel is surrounded by fat and/or connective tissue that attenuates sound (or ultrasound) much differently than does blood.

It does not matter that this incidentally- and acoustically-illuminated material is not moving. It affects the received acoustic signal in a manner that induces inaccuracy in the measured fluid flow rate, or volume. Namely, the material is not equally abundant (or sparse) at all regions of the acoustic paths. A transducer-to-transducer acoustic path directly through the center of the lumen, or blood vessel, likely couples very little of the differentially-attenuating material external to the lumen, or blood vessel. Portions of the transducer-to-transducer acoustic path proceeding through the side regions of the lumen, or blood vessel, are opposite. These portions of the acoustic path typically couple a good deal of the differentially-attenuating material that is external to the lumen, or blood vessel. In fact, it may be imagined that those portions of the acoustic path that just graze the regions of the lumen, or blood vessel, proximate to its wall proceed almost entirely through the material external to the lumen, or blood vessel, and only but a short ways through the flowing fluid, or blood.

The different attenuation provided to different portions of the acoustic path by the material surrounding the lumen, or blood vessel, serves to diminish those contributions to the flow signal resulting from fluid flow occurring within peripheral regions of the lumen relative to those contributions resulting from flow within the central region of the lumen. This means that flow within the peripheral regions of the lumen is not weighed as highly in the determination of average flow as flow occurring within the central region of the lumen (or, vice versa, that flow within the central region of the lumen is weighed more highly in the determination of average flow than is flow occurring within the peripheral regions of the lumen).

If regional flow within a lumen, or blood vessel, was everywhere the same, it might not matter if some regions were proportionately under, or over, represented in determination of an "average flow". Typically, however, the profile of flow velocity is stratified, with a slower velocity of fluid flow near the lumen walls where frictional resistance is experienced than at the lumen's center. Accordingly, such uneven weighting of flow from different regions of a lumen, or blood vessel, that is flowing fluid, or blood, at a stratified flow velocity profile as results from an even uniform acoustic illumination of the lumen and the attenuating material surrounding the lumen serves to inaccurately overestimate the measured average flow velocity, and flow volume. This effect is called "attenuation-based skew", and causes the average flow velocity to be overstated.

It will be further discussed in the aforementioned companion patent application for a VARIABLE ACOUSTIC ILLUMINATION OF A LUMEN FLOWING FLUID AT A STRATIFIED FLOW VELOCITY PROFILE IN ORDER TO MORE ACCURATELY DERIVE TRUE AVERAGE FLOW, PARTICULARLY DURING DOPPLER ACOUSTIC BLOOD FLOW MEASUREMENT that a Doppler acoustic flowmeter suffers from yet another type of error resulting from uniform acoustic illumination of (but a portion of) a lumen, or blood vessel, flowing fluid at a stratified profile of flow velocity. The measured average flow is again overstated. Both applications show that the utility of uniform illumination in acoustic fluid flow measurement must be reconsidered.

Normally the accuracy of an instrument such as a flowmeter is established by calibration against formerly-existing instruments, or against standards. The considerable inaccuracies of existing acoustic flowmeters in in-vivo blood flow measurement may have persisted because it has been difficult to calibrate such flowmeters in their actual environment of use. In other words, the simple expedient of observing how much fluid is accumulated in a reservoir after a set time in order to calibrate the measured flow is not available when the flow is that of blood in the closed system of a live animal.

SUMMARY OF THE INVENTION

The present invention contemplates varying the electro/acoustic or acousto/electric gain along the length of at least one acoustic transducer which, when situated across the width of a lumen flowing fluid in an acoustic flowmeter of either the transit time, or the continuous wave Doppler or pulsed Doppler, types, serves to transmit and/or receive acoustic signals through both (i) fluid flowing within the lumen and (ii) another material, generally surrounding the lumen, that presents a different acoustic attenuation than does the fluid. The variable, non-uniform, gain so established compensates for differing acoustic attenuation in different portions of the acoustic path.

In accordance with the invention either or both the electrical-to-acoustic, acousto/electric, gain of an transmitting transducer, or the acoustic-to-electrical, acousto/electric, sensitivity of a receiving transducer, is varied along the length of the transducer. Normally, and preferably, a single piezoelectric, or ferroelectric, transducer serves as both a transmitting transducer and a receiving transducer. Accordingly, it is normally the both electro/acoustic gain of a transducer acting at times as an acoustic transmitter, and the acousto/electric gain of the same transducer acting at other times as an acoustic receiver, that is varied. The product of the variable and non-uniform electro/acoustic and acousto/electric gains of the single transducer, or of two transducers, is preferably in inverse proportion to the acoustic attenuation that is presented to acoustic waves communicated along different portions of the acoustic path.

Accordingly, the amplitude of the electrical signal developed in and by the receiving acoustic transducer will be equal, and equally representative of fluid flow, everywhere along the length of such receiving transducer, and for all portions of the acoustic path. Regardless of whether it is the electro/acoustic gain of a transmitting transducer, or the acousto/electric gain of a receiving transducer, or the product of both such gains that is variable, and non-uniform, along the length of a transducer(s), the acoustic illumination of the flowing fluid within the lumen, or blood vessel, will be distinctly regionally non-uniform.

By the basic principles of a transit-time, or Doppler, acoustic flowmeter, an acoustic signal transmitted diagonally across the lumen will be variably time- and phase-delayed by the flowing fluid. Resultant to the non-uniformity of this acoustic illumination, and/or the acoustic reception, in accordance with the present invention, an electrical signal which is transduced from the variably time- and phase-delayed acoustic signal will have a substantially uniform amplitude at all points along the length of the acoustic receiver. When the time and/or phase delay of this signal is subsequently electronically interpreted as a measurement of the velocity of the flowing fluid, the uniform amplitude of the signal will help to prevent that attenuation-based skew resulting from different attenuations along different portions of the acoustic transmission path should induce error in the measured average fluid flow.

Particularly during in-vivo acoustic measurement of blood flow, a blood vessel is normally surrounded by a material, typically fat or connective tissue, that attenuates acoustic waves differently than does the blood. In accordance with the present invention, this blood vessel and its surrounding tissue is variably, and non-uniformly, acoustically illuminated. The variable acoustic illumination serves to compensate for the differing acoustic attenuation presented by the blood and the tissue, and to produce a more accurate flow volume, or rate, determination.

The compensation for varying acoustic attenuation realized by the varying acoustic gain, and (typically) the non-uniform acoustic illumination, in accordance with the present invention is applicable to both transit-time flowmeters and to Doppler flowmeters of either the continuous wave or pulsed types. However, and as is particularly taught in the companion patent application for NON-UNIFORM ACOUSTIC ILLUMINATION OF A LUMEN FLOWING FLUID AT A STRATIFIED FLOW VELOCITY PROFILE IN ORDER TO MORE ACCURATELY DERIVE TRUE AVERAGE FLOW, PARTICULARLY DURING DOPPLER ACOUSTIC BLOOD FLOW ANALYSIS, a transducer within a Doppler flowmeter may also be further compensated. This further compensation accounts for a different average velocity of fluid flow occurring within the acoustically illuminated volume (the "sample volume") of the lumen than occurs within the lumen as a whole. This, and other, spatially selectively variable transducer gains are multiplied with the non-uniform transducer gain in accordance with the present invention.

The magnitude(s) of any "compensation" to uniform acoustic illumination, and the appropriate non-uniform acoustic gain, along the length of the acoustic transducer and across the substantial width of the lumen within which fluid flow is to be measured, may be mathematically or empirically determined. Particularly for acoustic blood flow measurement, the acoustic attenuation of various surrounding tissues, particularly including fat, is well known.

The desired non-uniform acoustic gain is achieved by an elongate sonic transducer, typically a piezoelectric element, that is physically shaped and contoured so as to have a non-uniform acoustic output and/or a non-uniform acoustic sensitivity (i.e., acoustic input) along its physical length.

These and other aspects and attributes of the present invention will become increasingly clear upon reference to the following drawings and accompanying specification.

DESCRIPTION OF THE PREFERRED EMBODIMENT

The present invention is particularly useful in the acoustical measurement of blood flow. This is because ultrasound must often pass through several types of tissue having vastly different acoustical properties during either transit time, or Doppler, acoustic blood flow measurement. These differing acoustic properties, particularly acoustical attenuation, cause, if not properly compensated for, significant errors in flow measurement.

Figure 1:
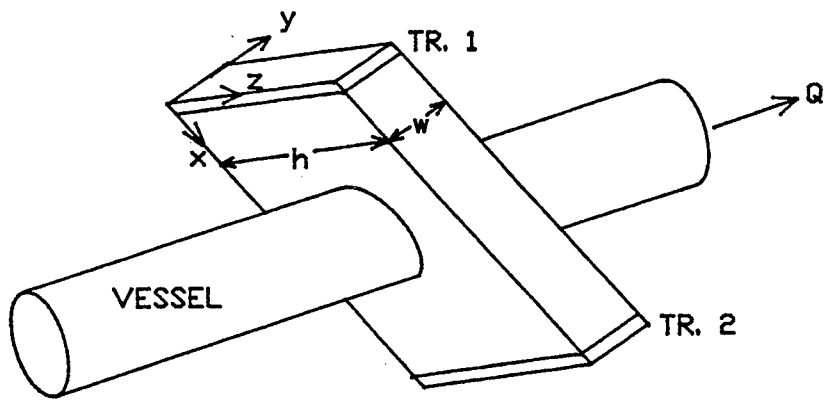
FIG. 1 is a diagrammatic representation of the geometry of two transducers of a prior art transit time acoustic flowmeter, the transducers providing constant-intensity full-vessel acoustic illumination of a lumen, or blood vessel; the transit time of the beam being proportional to the average rate of flow of the fluid intersecting the beam and the lumen's dimensions.
Figure 2:
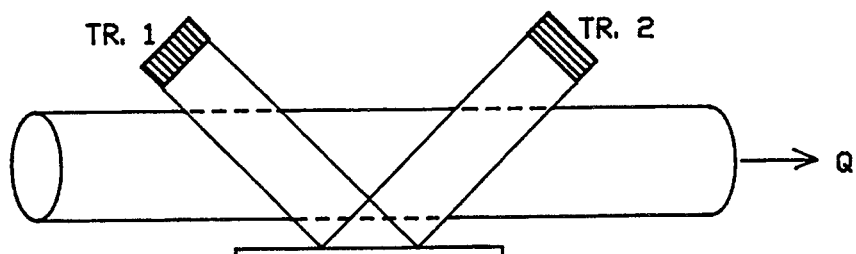
FIG. 2 is a diagrammatic representation of the geometry of a reflected acoustic pathway in a prior art transit time acoustic flowmeter.
Figure 3:
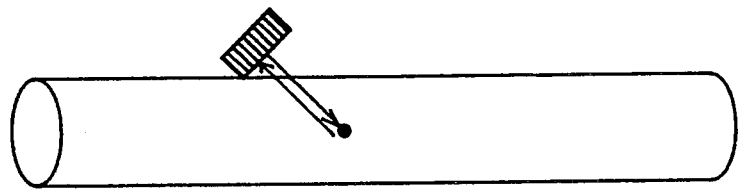
FIG. 3 is a diagrammatic representation of the geometry of an acoustic pathway in a prior art single-transducer Doppler acoustic flowmeter.
Figure 4:
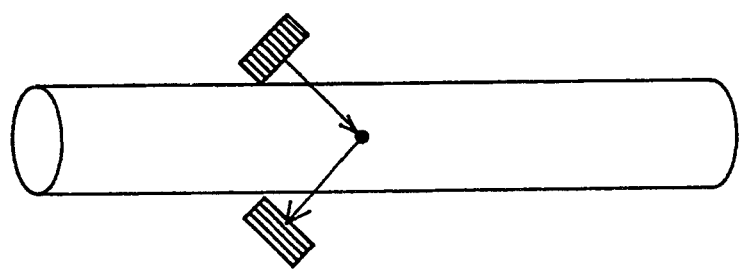
FIG. 4 is a diagrammatic representation of the geometry of an acoustic pathway in a prior art dual-transducer Doppler acoustic flowmeter.
Figure 5:
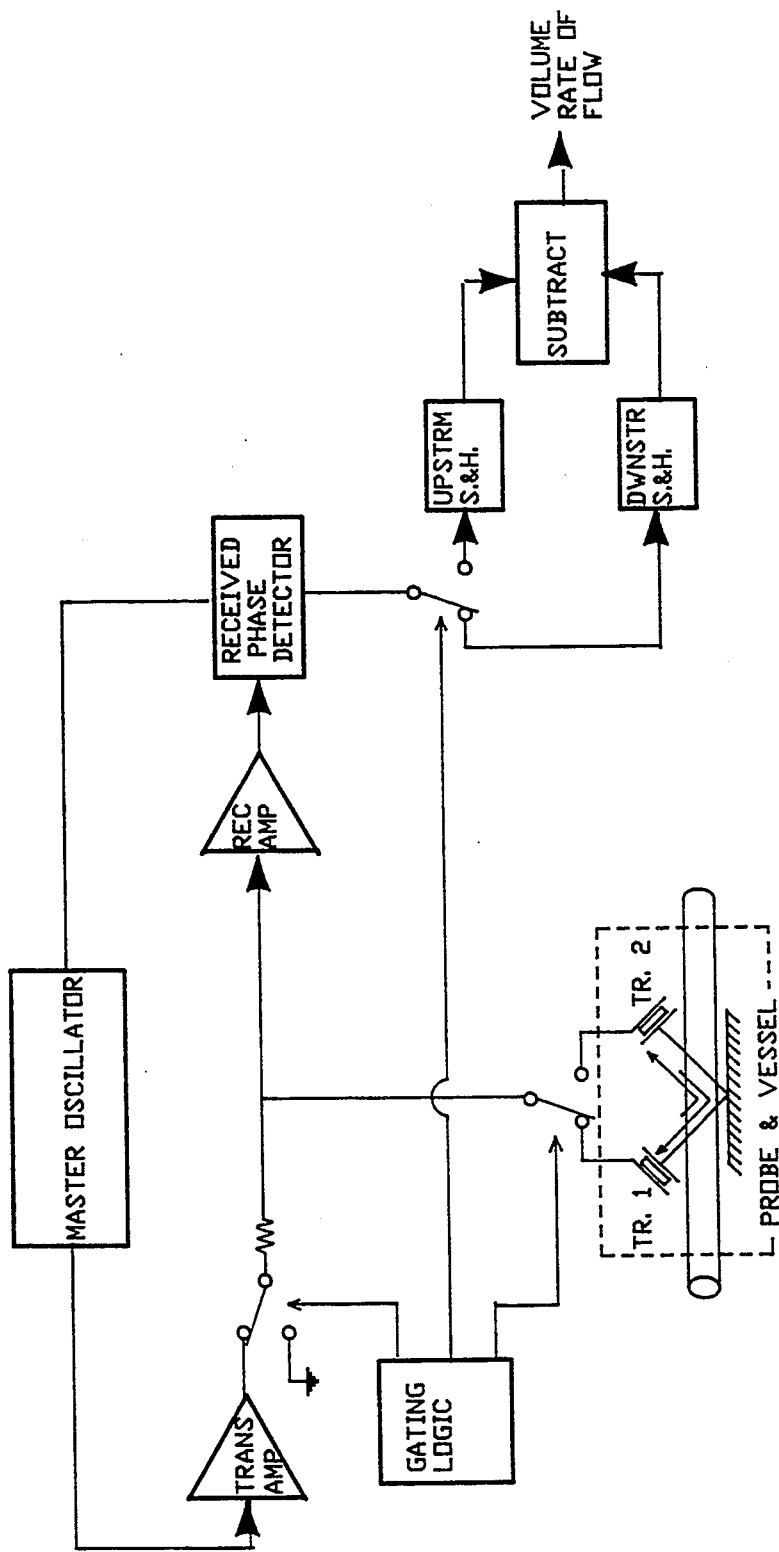
FIG. 5 is an electrical schematic block diagram of a prior art transit time flowmeter where upstream and downstream flows are alternately measured.
Figure 6:
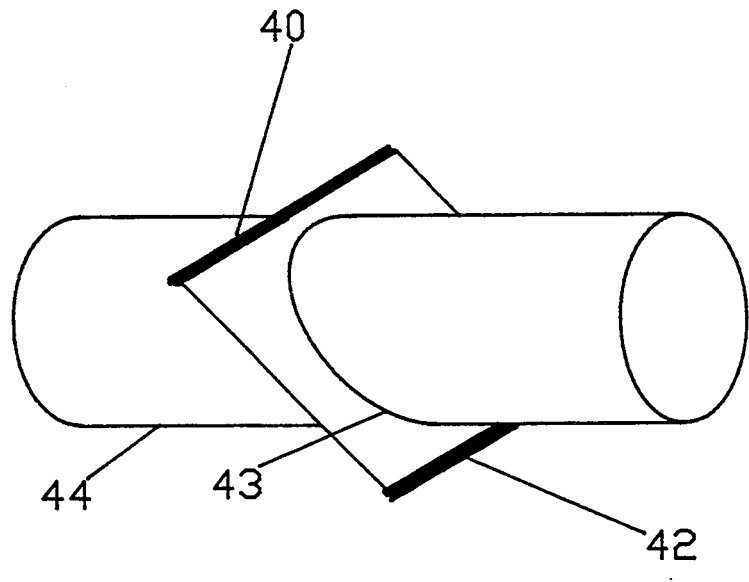
FIG. 6 is an expanded diagrammatic representation, similar to FIG. 1, of the geometry of two variable gain acoustic transducers the present invention in use about a lumen for transit time acoustic flow measurement.

Rader described a transit time volume flow measuring system based on a thin "line transducer" of sufficient length to span the width of the vessel in his seminal paper "A diameter independent blood flow measurement technique" appearing in Medical Instrumentation, Vol. 10, No. 4 for July-August, 1976 at pages 185–188. This prior art configuration of a pair of line transducers 40, 42 is shown in FIG. 1. Such paired transducers 70 acoustically illuminate, or "insonicate", each portion of the flow cross section 43 of a lumen, or blood vessel, 44 so that each portion of the flow profile is sampled. Similar configurations have been described by Lynnworth in U.S. Pat. Nos. 3,575,050 and 3,906,791 for the measurement of flow in general conduits, and by Drost in U.S. Pat. Nos. 4,227,407 and 4,391,124 with specific applications to the measurement of blood flow in-vivo.

Figure 7:
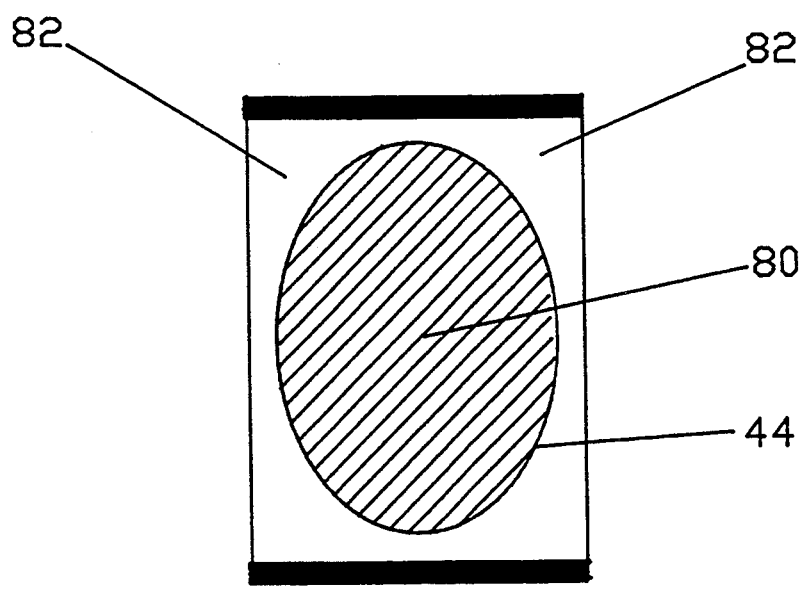
FIG. 7 is a diagrammatic representation of the cross-section of a blood vessel and surrounding fat or connective tissue located in the acoustic path between the two variable-gain transducers previously seen in FIG. 6.
Figure 8:
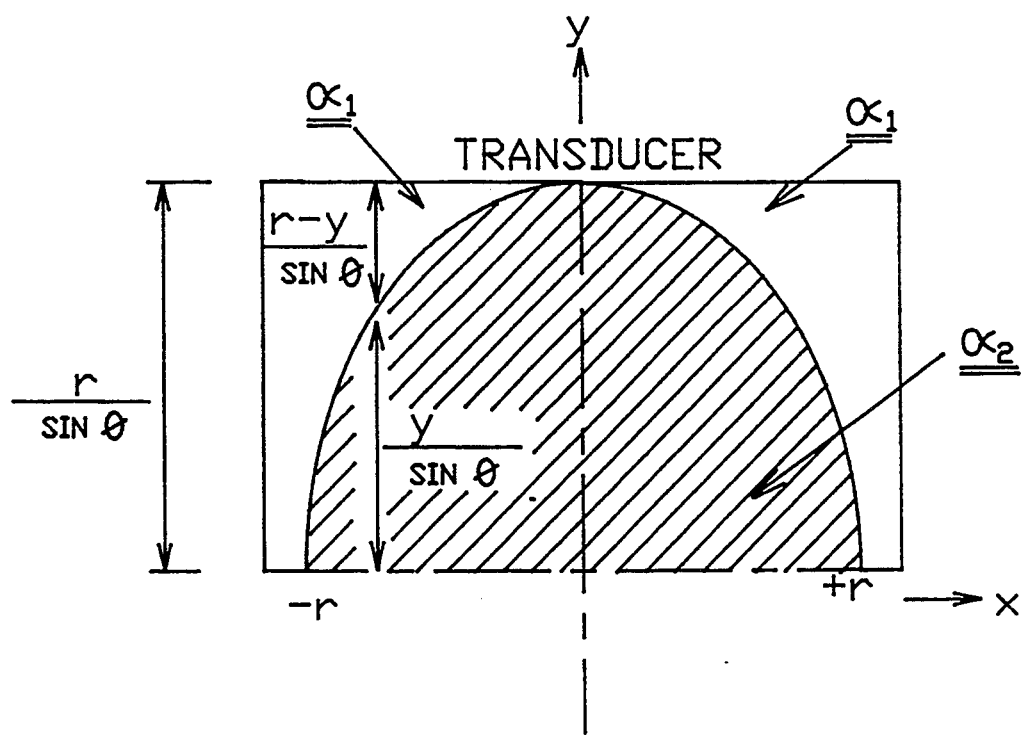
FIG. 8 is a graphical representation of a diagonal slice through a lumen or blood vessel of radius "r", showing the attenuation experienced by portions of an acoustic path through the lumen when it is flowing fluid of an attenuation constant $a_2$ at a stratified profile of flow velocity, the lumen being surrounded by material of an attenuation constant $a_1$.
Figure 9:
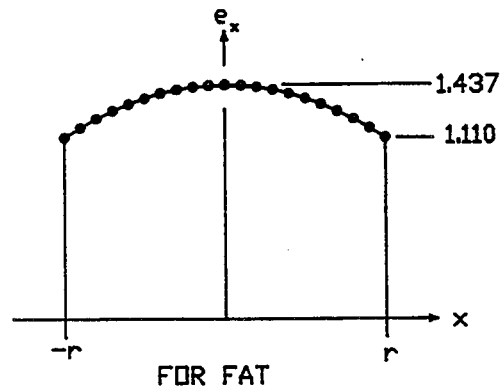
FIG. 9 is a graph of the solution to the equation of the attenuation produced by surrounding fat for various acoustic paths through a blood vessel.

The receiving transducer 40 (or 42, as the case may from time to time may be) in each of these configurations sums the composite portions of the received ultrasonic signal to form a time domain received signal. As can be seen in FIGS. 7–9, each portion of the received signal travels a portion of its path in the flowing fluid 80 (shown in the cross-section 43) and a portion of its path in surrounding tissues 82.

The tissues 82 surrounding a blood vessel 44 may be any of several types depending on the circumstances of the procedure. They can be: smooth muscle of the vessel wall, fat, muscle, connective tissue, scar, etc. These tissues 82 generally have velocities of sound which are similar to that of blood, but their attenuation values can be significantly different than that of blood. For instance, on a blood vessel 44 such as the root of the aorta, pads of fat are normally found on the aorta's exterior surface.

The tissues 82 surrounding the blood vessel 44 are not moving, and consequently contribute only a fixed time delay to the combined signal. These surrounding tissues 82 do, however, attenuate the portion of the signal passing through them. Due to the geometry of the paths, the sound passing through edges of the blood vessel 44 passes through relatively more surrounding tissue 82, and suffers greater attenuation, than does the sound passing through the center of the blood vessel 44. The result is that the flow velocity components from the off-axis portion of the flow profile are under-represented in the received composite signal. These areas represent the largest portion of the total flow cross section which contains the slower moving portions of the flow. The result the non-equal attenuation is that the received signal will over-estimate the "average velocity".

In accordance with the present invention, the measurement of blood flow utilizing implanted transducers is improved by varying the electro/acoustic, and/or the acousto/electric, gain of a transducer along its length. The transducer is positioned lengthwise across the width of the blood vessel 44 during acoustic flow measurement. This technique of the present invention uses biased, non-uniform acoustic illumination ("insonication") of the flow path to compensate for attenuation of the surrounding tissues.

For example, fat has an attenuation factor approximately 30% higher than that of blood. If the space between the piezoelectric element and the blood vessel is filled with fat, the flow components in the outer portions of the flow cross section will be attenuated by as much as 30%, as shown in FIGS. 8 and 9. An elongate transducer 40, a lumen or blood vessel 43 flowing fluid of attenuation constant $\alpha_1$ at a stratified profile of flow velocity, a material 82 of attenuation constant $\alpha_2$ surrounding the lumen 43, and acoustic paths from the transducer through lumen and its surrounding material are diagrammatically represented in FIG. 8. A graph of the attenuation effect on different portions of the acoustic path through the lumen or blood vessel 43 flowing the fluid of an attenuation constant $\alpha_2$ surrounded by the material 82 of an attenuation constant $\alpha_1$ is shown in FIG. 9.

The acoustic environment experienced by a linearly straight transducer used in radial touching contact tight against a blood vessel that is otherwise surrounded by fat is shown in FIGS. 6–9. The design of an attenuation-compensated transducer would transpire, by example, as follows:

$$\alpha_2 = 0.91 \frac{dB}{cm} @ 5 \text{ Mhz}$$
$$= 10^{(\frac{.91}{20})}$$
$$= 1.110 \text{ BLOOD}$$

$$\alpha_1 = 3.15 \frac{dB}{cm} @ 5 \text{ Mhz}$$
$$= 10^{(\frac{3.15}{20})}$$
$$= 1.437 \text{ FAT}$$

Comparing the two results yields:

$$\frac{1.437}{1.110} = 1.30$$
$$= 30\% \text{ HIGHER ATTENUATION FOR FAT}$$

The acoustical path is represented by an elliptical slice through the lumen (as shown in FIG. 7) where r is the radius of the lumen.

Let $e_x$ equal the amplitude of the received signal at a point on the x axis between $-r$ and $+r$. Let e equal the transmitted signal level at the transmitting crystal transducer. Then:

$$\frac{e_x}{e} = \left[\left(\frac{r}{\text{SIN}\Theta} - \frac{y}{\text{SIN}\Theta}\right)\alpha_1 + \frac{y}{\text{SIN}\Theta}\alpha_2\right]$$

$$\frac{e_x}{e} = \left[\frac{r}{\text{SIN}\Theta}\alpha_1 + \frac{y}{\text{SIN}\Theta}(\alpha_2 - \alpha_1)\right]$$

For the case of a circular blood vessel (lumen):

$$y = \sqrt{r^2 - x^2}$$

The equations then solve:

$$\frac{e_x}{e} = \left[\frac{r}{\text{SIN}\Theta}\alpha_1 + \left(\sqrt{\frac{r}{\text{SIN}\Theta} - x^2}\right)(\alpha_2 - \alpha_1)\right]$$

Figure 10:
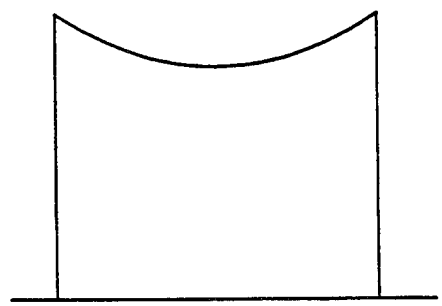
FIG. 10 is a graph showing the variable electro/acoustic, or acousto/electric, gain along the length(s) of a transducer(s) necessary to compensate for the attenuation of fat surrounding a blood vessel as graphed in FIG. 9.

This solution of this equation for the effects of attenuation produced by fat 82 surrounding the lumen 43 (shown in FIGS. 6–8) for various portions of an acoustic path through a blood vessel is shown in FIG. 9. A complimentary graph of the variable electro/acoustic, or acousto/electric, gain(s) along the length(s) of a transducer(s) that is (are jointly) necessary to compensate for the attenuation of the fat surrounding the blood vessel is shown in FIG. 10.

The acoustical output of a piezoelectric transducer is a function of several factors including the area of the transducer, the strength of the electric field across the transducer, and the efficiency of the transducer. For a transducer of given size and efficiency, the strength of the electric field regionally within the transducer is a function of the extent of one of both of the metal electrodes on opposite faces of the transducer.

Figure 11:
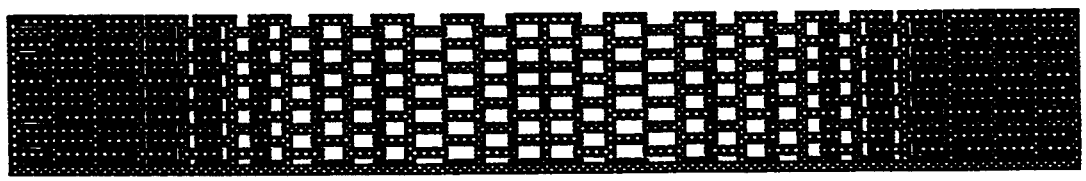
FIG. 11 is a diagrammatic representation of a transducer having that variable electro/acoustic, or acousto/electric, gain along its length that was previously seen in the graph of FIG. 10; which variable gain is obtained by selective electrode metalization removal, or "shading".

A rectangular transducer projects a beam which has a rectangular pattern with approximately uniform insonication in the near field. Likewise an irregularly shaped transducer will project a pattern which mimics the shape of the transducer in the near field. A diagrammatic representation of the patterned metallization of a transducer having that particular variable electro/acoustic, or acousto/electric, gain along its length which was graphed in FIG. 10 is shown in FIG. 11. The metallization on the two faces of a transducer crystal is typically silver. The transducer body is typically barium titonate zirconate. The metallization is either patterned, or etched, to varying density. Either, or preferably both, electrodes may be selectively metallized. Lynnworth calls the process of so adjusting the spatial gain of a transducer "shading".

The transducer responds to both to emit, and to receive, more strongly in the regions of more extensive, or complete, metallization. In FIG. 11 this may be observed to occur proximately to the transducer's two ends, meaning that during acoustic emission the acoustic field amplitude will be highest at these locations. The long axis of the transducer shown in FIG. 11 is normally as long as the interior diameter of the lumen, or blood vessel, for which flow is measured. The transducer, with its spatially variable gain, is positioned with its long axis across the lumen, or blood vessel, and its surrounding material, or tissue. This is, of course, the relationship desired in order to compensate for the differing attenuations at different portions of the acoustic path.

In accordance with the preceding discussion, still further adaptations and embodiments of the present invention will suggest themselves to a practitioner of the electro-acoustic arts. Many times "portions of a [single] acoustic path" are spoken of, equivalently and interchangeably, as being separate "acoustic paths". This suggests that the principles of the present invention are equally applicable to one, or to many, acoustic paths, and to each acoustic path in proportion to the attenuations differently experienced by sound transmitted and received thereon.

In accordance with the preceding explanation, the present invention should be interpreted broadly, and in accordance with the following claims only, and not solely in accordance with that particular embodiment within which the invention has been taught.

What is claimed is:

1. An acoustic flowmeter for measuring a flow of a fluid within a lumen that is surrounded by material that attenuates acoustic waves differently than does the fluid, the flowmeter comprising:

an elongate acoustic transducer means, having a length subtending the width of the lumen and the material surrounding the lumen, and having a predetermined electro-acoustic/acousto-electric gain that varies in magnitude along its length, for, at times responsive to electrical energization, acoustically illuminating both the lumen and the lumen's surrounding material at an acoustic intensity that is spatially variable substantially in accordance with differing acoustic attenuations of different acoustic paths that pass through differing amounts of the lumen and the material surrounding the lumen, and for, at other times, producing an electrical signal responsive to receipt of the spatially variable acoustic illumination via the acoustic paths of differing acoustic attenuation passing through both the lumen and the lumen's surrounding material; and electrical energizing means for electrically energizing the transducer means so that, responsively thereto, the transducer means will both spatially variably acoustically illuminate the lumen and its surrounding material and, resultant to such illumination, produce the electrical signal;

wherein, because of the electro-acoustic/electro-acoustic gain that is of a predetermined variable magnitude along the length of the transducer means, the produced electrical signal will be of substantially equal amplitude at all points along the length of the transducer means nonetheless that different acoustic paths both pass through differing amounts of the flowing fluid and surrounding material and are, in accordance with such passages, differently acoustically attenuated;

wherein the electro-acoustic/acousto-electric gain that is of a predetermined variable magnitude along the length of the transducer means compensates for the differing acoustical attenuations of the different acoustic paths;

wherein the transducer means is attenuation-compensated.

2. (Amended) The acoustic flowmeter according to claim 1 of a transit time type wherein the elongate acoustic transducer means comprises:

a pair of transducers, at least a transmitting one or a receiving one of which pair of transducers has a the electro-acoustic/acousto-electric gain that is of a predetermined variable magnitude along its length.

3. The acoustic flowmeter according to claim 2 wherein the pair of acoustic transducers of the transit-time acoustic flowmeter are suitably sized and shaped so as to be located within a living animal obliquely across a blood vessel for in-vivo blood flow measurement;

wherein the electro-acoustic/acousto-electric gain, or attenuation compensation, that is of a predetermined variable magnitude along the length of at least the one of the pair of acoustic transducers compensates for the differing acoustic attenuations of different acoustic paths that pass through differing amounts of blood and tissue surrounding the blood vessel and that are, in accordance with such passages, differently acoustically attenuated.

4. The acoustic flowmeter according to claim 1 of a Doppler type wherein the elongate acoustic transducer means comprises:

a single acoustic transducer for, at separate times, both transmitting and receiving acoustic signals.

5. The acoustic flowmeter according to claim 2 wherein the single acoustic transducers of the Doppler acoustic flowmeter is suitably sized and shaped so as to be located within a living animal at an oblique angle to a blood vessel for in-vivo blood flow measurement;

wherein the electro-acoustic/acousto-electric gain, or attenuation compensation, that is of a predetermined variable magnitude along the length of the acoustic transducer compensates for the differing acoustical attenuations of different acoustic paths that pass through differing amounts of blood and tissue surrounding the blood vessel and that are, in accordance with such passages, differently acoustically attenuated.

6. The acoustic flowmeter according to claim 1 of a Doppler type wherein the elongate acoustic transducer means comprises:

a pair of transducers, at least a transmitting one or a receiving one of which pair of transducers has the electro-acoustic/acousto-electric gain that is of a predetermined variable magnitude along its length.

7. The acoustic flowmeter according to claim 6 wherein the two acoustic transducers of the Doppler acoustic flowmeter are suitably sized and shaped located within a living animal obliquely across a blood vessel for in-vivo blood flow measurement;

wherein the electro-acoustic/acousto-electric gain, or attenuation compensation, that is of a predetermined variable magnitude along the length of at least the one of the two acoustic transducers compensates for the differing acoustical attenuation of different portions of the acoustic path that both pass through differing amounts of blood and surrounding tissue and are, in accordance with such passage, differently acoustically attenuated.

8. The acoustic flowmeter according to claim 6 wherein the pair of transducers of the Doppler acoustic flowmeter are located on opposite sides of the lumen so that fluid flow within only a portion, less than the entirety, of the entire cross-sectional area of the lumen is acoustically measured.

9. The acoustic flowmeter according to claim 8 applied to a lumen within which the velocity of fluid flow is stratified
wherein the at least one of transducer of the pair of such transducers of the Doppler acoustic flowmeter has an electro-acoustic/acousto-electric gain along its length that is not only variable substantially so as to compensate for the differing attenuation of the acoustic wave by the flowing fluid and the surrounding material, but is also, additionally, non-uniform so as to compensate for a differing average rate of fluid flow occurring within the acoustically illuminated portion of the lumen than occurs within the entire lumen;
wherein the gain of the sonic transducer is area-compensated for the stratified fluid flow as well as being attenuation-compensated for the differing acoustical attenuation of the different portions of the acoustic path.

10. The acoustic flowmeter according to claim 9 wherein the two acoustic transducers of the Doppler acoustic flowmeter type are suitably sized and shaped so as to be located within a living animal for in-vivo measurement of blood flow within a blood vessel;
wherein the electro-acoustic/acousto-electric gain, or attenuation compensation, that is of a predetermined variable magnitude along the length of at least the one of the two acoustic transducers compensates for the differing acoustical attenuations of different acoustic paths that both pass through differing amounts of blood and surrounding tissue and are, in accordance with such passages, differently acoustically attenuated; and
wherein the electro-acoustic/acousto-electric gain, or area compensation, that is of a predetermined variable magnitude along the length of at least the one of the two acoustic transducers further compensates for the differing average rate of blood flow occurring within the acoustically-illuminated portion of the blood vessel's cross-sectional area for which flow is acoustically measured than occurs within the entire cross-sectional area of the blood vessel.

11. The acoustic flowmeter according to claim 1 wherein the elongate acoustic transducer means comprises:
a transmitting transducer having a non-uniform electro-acoustic gain along its length; and
a receiving transducer having a substantially uniform acousto-electric gain along its length; and
wherein the non-uniform electro-acoustic gain of the transmitting transducer compensates for the differing acoustic attenuations of the different acoustic paths.

12. The acoustic flowmeter according to claim 1 wherein the elongate acoustic transducer means comprises:
a transmitting transducer having a substantially uniform electro-acoustic gain along its length; and
a receiving transducer having a non-uniform acousto-electric gain along its length; and
wherein the non-uniform acousto-electric gain of the receiving transducer compensates for the differing acoustic attenuations of the different acoustic paths.

13. The acoustic flowmeter according to claim 1 wherein the pair of elongate acoustic transducers comprises:
a transmitting transducer having a non-uniform electro-acoustic gain along its length; and
a receiving transducer having a non-uniform acousto-electric gain along its length; and
wherein the non-uniform electro-acoustic gain of the transmitting transducer serves, when multiplied with the nonuniform acousto-electric gain of the receiving transducer, to jointly compensate for the differing acoustic attenuations of the different acoustic paths.

14. A method of acoustic in-vivo measurement of a flow of blood within a blood vessel that is surrounded by tissue that attenuates acoustic waves differently than does blood, the method comprising:
positioning a pair of elongate acoustic transducers of an acoustic flowmeter, at least one of which pair of transducers has a non-uniform electro-acoustic/acousto-electric gain along its length, so as to acoustically illuminate both the blood vessel and its surrounding tissue; and
electrically energizing a transmitting one of the pair of transducers so that, responsively thereto, a receiving one of the pair of transducers will, due to the non-uniform electro-acoustic/electro-acoustic gain of at least one of the pair of transducers, at all points along the length thereof produce an electrical signal the amplitude of which is substantially uniform nonetheless that different acoustic paths between the pair of transducers pass through differing amounts of blood and surrounding tissue and are, in accordance with such passage, differently acoustically attenuated;
wherein the non-uniform electro-acoustic/acousto-electric gain of at least the one of the pair of transducers compensates for the differing acoustical attenuation of the different acoustic paths;
wherein the at least the one of the pair of transducers is attenuation-compensated.

15. The acoustic blood flow measurement method according to claim 14 wherein the positioning comprises:
locating the pair of acoustic transducers obliquely across the blood vessel to perform transit-time acoustic flow measurement.

16. The acoustic blood flow measurement method according to claim 14 wherein the positioning comprises:
locating the pair of acoustic transducers diagonally across from each other on opposite sides of the blood vessel to perform Doppler acoustic flow measurement.

17. The acoustic blood flow measurement method according to claim 16 applied to a blood vessel within which blood flow velocity is stratified
wherein the located pair of acoustic transducers of the Doppler acoustic flowmeter, at least one of which transducers has an electro-acoustic/acousto-electric gain along its length in order to compensate for the differing attenuation of the acoustic wave by the blood and the surrounding tissue, is also, further, of at least one transducer having still further non-uniformity in the electro-acoustic-/acousto-electric gain along its length so as to also, additionally, compensate for a differing average rate of blood flow within an acoustically sampled portion of the of the blood vessel's cross-sectional area than occurs within the blood vessel's entire cross-sectional area;

wherein the gain of the pair of acoustic transducers is area compensated for the stratified fluid flow as well as attenuation-compensated for the differing acoustical attenuations of the different acoustic paths.

18. The acoustic blood flow measurement method according to claim 14 wherein the positioning is of a pair of elongate acoustic transducers the transmitting one of which has a non-uniform electro-acoustic gain along its length while the receiving one of which has a substantially uniform acousto-electric gain along its length; and wherein the non-uniform electro-acoustic gain of the transmitting one of the pair of transducers compensates for the differing acoustical attenuations of the different acoustic paths.

19. The acoustic blood flow measurement method according to claim 14 wherein the positioning is of a pair of elongate acoustic transducers the receiving one of which has a non-uniform acousto-electric gain across its length while the transmitting one of which has a substantially uniform electro-acoustic gain along its length; and wherein the non-uniform acousto-electric gain of the receiving one of the pair of transducers compensates for the differing acoustical attenuations of the different acoustic paths.

20. The acoustic blood flow measurement method according to claim 14 wherein the positioning is of a pair of finite-width acoustic transducers of an acoustic flowmeter each of which transducers has a non-uniform electro-acoustic/acousto-electric gain across its finite width; and wherein the non-uniform electro-acoustic gain of a transmitting one of the pair of transducers serves, when multiplied with the non-uniform electro-acoustic gain of the receiving one of the pair of transducers, to jointly compensate for the different acoustical attenuations of the different paths.

21. An acoustic transit-time flowmeter for in-vivo measurement of a flow of blood within a blood vessel that is surrounded by tissue that attenuates acoustic waves differently than does blood, the flowmeter comprising:

a pair of elongate acoustic transducers, at least one of which pair of transducers has a non-uniform electro-acoustic/acousto-electric gain along its length, positionable so as to acoustically illuminate both a blood vessel and its surrounding tissue that attenuates acoustic waves differently than does blood; and means for electrically energizing a transmitting one of the pair of transducers so that, responsively thereto, a receiving one of the pair of transducers will, due to the non-uniform electro-acoustic-/acousto-electric gain of at least one of the pair of transducers, produce an electrical signal the amplitude of which is substantially uniform at all points along the receiving transducer's length nonetheless that different acoustic paths between the transducers pass through differing amounts of blood and surrounding tissue and are, in accordance with such passages, differently acoustically attenuated;

wherein the non-uniform electro-acoustic/acousto-electric gain of at least one of the pair of transducers compensates for the different acoustical attenuations of the different acoustic paths.

22. A sonic transmitter for use in an acoustic flowmeter measuring a flow of a fluid in a conduit that is at least partially embedded within a material that attenuates acoustic waves differently than does the fluid flowing in the conduit, the sonic transmitter comprising:

an elongate sonic transmitter means emitting acoustic waves along its length, the acoustic emissions being non-uniform in amplitude in inverse proportion to the differing attenuation presented to the acoustic waves by the flowing fluid and by the material, in combination, at each point of acoustic emission along the length of the sonic transmitter means;

a housing for holding the sonic transmitter means in positional proximity to, and at an angular orientation relative to, the conduit flowing fluid so that its non-uniform acoustic emissions are in substantial spatial registration with the differing attenuation to acoustic waves that is presented to the sonic transmitter by the combination of the flowing fluid and the material;

wherein, when a sonic receiver is positioned on an opposite side of the conduit to the sonic transmitter means, detection in and by the sonic receiver means of the acoustic waves emitted by the sonic transmitter means will produce an electrical signal;

wherein the amplitude of the electrical signal produced by the sonic receiver will be, at least partially, a function of the attenuation of the emitted acoustic wave during its passage through the combination of flowing fluid and material;

wherein because the acoustic emission along the length of the sonic transmitter means is non-uniform in inverse proportion to the differing attenuation to acoustic waves that is presented by the combination of the fluid and the material at each point of acoustic emission along the length of the sonic transmitter means, the produced electric signal will weigh the rates of fluid flow though all regions of the conduit substantially equally.

23. The sonic transmitter according to claim 22 used in a transit time acoustic flowmeter, wherein a time delay of the electrical signal produced by the sonic receiver relative to the electrical excitation of the sonic transmitter means will be a function of a time of transit of the emitted acoustic waves through the flowing fluid of the conduit, which time of transit is related to the velocity of fluid flow within the conduit.

24. The sonic transmitter according to claim 22 used in a Doppler acoustic flowmeter, wherein a shift in phase of the electrical signal produced by the sonic receiver relative to the electrical excitation of the sonic transmitter means will be a function of phase-shifting occurring during the transit of the emitted acoustic waves through the flowing fluid of the conduit, which phase-shifting is related to the velocity of fluid flow within the conduit.

25. A sonic receiver for an acoustic flowmeter used to measure a flow of a fluid in a conduit that is at least partially embedded within a material that attenuates acoustic waves differently than does the fluid flowing in the conduit, the sonic receiver comprising:

- an elongate sonic receiver means responsive to acoustic waves received along its length for producing an electrical signal, the sonic receiver means having along its length a non-uniform acousto-electric sensitivity that is in inverse proportion to the differing attenuation of acoustic waves that is presented by the flowing fluid and by the material, in combination, at each point of acoustic reception along the length of the sonic receiver means;
- a housing for holding the sonic receiver means in positional proximity to, and at an angular orientation relative to, a conduit flowing fluid so that the non-uniform acousto-electric sensitivity of the sonic receiver means is in substantial spatial registration with the differing attenuation of acoustic waves that is presented to the sonic receiver by the combination of the flowing fluid and the material;
- wherein, when a sonic transmitter is positioned on an opposite side of the conduit to the sonic receiver means and electrically excited so as to emit an acoustic wave, a detection in and by the sonic receiver means of the acoustic wave will produce an electrical signal;
- wherein an amplitude of the electrical signal produced at each point along the sonic receiver means will be, at least partially, a function of the attenuation of the emitted acoustic wave during its passage through the combination of flowing fluid and material;
- wherein because the acousto-electric sensitivity of the sonic receiver means to the acoustic wave received along its length is non-uniform in inverse proportion to the differing attenuation of acoustic waves that is presented by the combination of the fluid and the material at each point of acoustic reception along the length of the sonic receiver means, the produced electric signal will weigh the rates of fluid flow though all regions of the conduit substantially equally.

26. The sonic receiver according to claim 25 used in a transit time acoustic flowmeter, wherein a time delay of the electrical signal produced by the sonic receiver means relative to the electrical excitation of the sonic transmitter will be a function of a time of transit of the emitted acoustic waves through the flowing fluid of the conduit, which time of transit is related to the velocity of fluid flow within the conduit.

27. The sonic receiver according to claim 25 used in a Doppler acoustic flowmeter, wherein a shift in phase of the electrical signal produced by the sonic receiver means relative to the electrical excitation of the sonic transmitter will be a function of phase-shifting occurring during the transit of the emitted acoustic waves through the flowing fluid of the conduit, which phase-shifting is related to the velocity of fluid flow within the conduit.

* * * * *